United States Patent
DiGiovanni et al.

(10) Patent No.: US 6,513,994 B1
(45) Date of Patent: Feb. 4, 2003

(54) TESTING OPTICAL FIBER SPLICES

(75) Inventors: David John DiGiovanni, Montclair, NJ (US); John Edwin Graebner, Short Hills, NJ (US); Sun-Young John Kwak, Fort Lee, NJ (US)

(73) Assignee: Fitel USA Corp., Norcross, GA (US)

( * ) Notice: Subject to any disclaimer, the term of this patent is extended or adjusted under 35 U.S.C. 154(b) by 0 days.

(21) Appl. No.: 09/561,035

(22) Filed: Apr. 28, 2000

(51) Int. Cl.⁷ .............................................. G02B 6/255
(52) U.S. Cl. ............................ 385/95; 385/52; 356/73.1
(58) Field of Search ........................... 385/15, 31, 95, 385/96, 97, 98, 99, 52, 90; 356/73.1; 73/190; 250/227.24

(56) References Cited

U.S. PATENT DOCUMENTS 3,575,048 A * 4/1971 De Benedictis .............. 73/190

H1426 H * 4/1995 Toeppen ...................... 385/15

* cited by examiner

Primary Examiner—Cassandra Spyrou
Assistant Examiner—Euncha Cherry
(74) Attorney, Agent, or Firm—Peter V. D. Wilde; Thomas, Kayden, Horstemeyer & Risley L.L.P.

(57) ABSTRACT

The specification describes a technique for evaluating optical fiber splices. The essence of the technique involves detecting thermal power emanating from the fiber splice as the result of absorption of the light carried by the fiber. The technique is particularly suited for cladding pumped lasers wherein the splicing operation may introduce excessive absorption of pump laser radiation and excessive heating at the splice locale.

7 Claims, 2 Drawing Sheets

TESTING OPTICAL FIBER SPLICES

FIELD OF THE INVENTION

This invention relates to test techniques for measuring loss in optical fiber splices. It is specially suited for testing fiber splices in laser devices that are pumped via a cladding layer.

BACKGROUND OF THE INVENTION

Rare-earth-doped fiber lasers are finding a variety of uses in optical communication systems where they can be integrated effectively with fiber links, and active fiber devices such as erbium fiber amplifiers. These lasers are frequently dual clad structures that are end pumped with inexpensive multi-mode lasers, such as GaAlAs. See e.g., L. Zenteno, "High-Power Double-Clad Fiber Lasers", *Journal of Lightwave Technology*, Vol. 11, No. 9, pp. 1435–1446, September 1993. In a preferred structure, a threshold level of germanium dopant is incorporated into the fiber core in order to write Bragg gratings in the core and thereby create a laser cavity. Dopants such as aluminum are added to aid in solubilizing the active rare earth ions and prevent crystallization of the aluminum, and consequent scattering losses in the fiber core. See my copending patent application Ser. No. 08/908,258, filed Aug. 7, 1997, incorporated herein by reference.

The active section of a dual clad cladding pumped laser device is typically spliced to a pigtail connected to the pump laser. This splice carries relatively intense optical radiation and should be of high quality to avoid excessive losses. In prior art laser technology, the quality of the splice between the pump laser and the active laser fiber typically is not generally regarded as critical since losses at this point are not signal losses. Therefore, sophisticated splice loss measurement techniques that are available for splices in the signal path typically would not be applied to the pump pigtail splice. However, we have discovered that defective pump pigtail splices may be very significant because they often produce excessive heating in the vicinity of the splice. This heating will age the optical properties of the fiber prematurely, and may result in darkening or even melting of the fiber coating. Excessive heating is due to a variety of factors which contribute to optical absorption at the splice. Conventional optical integrating splice test apparatus will not detect the energy from absorption and excessive heating.

STATEMENT OF THE INVENTION

For optical fiber splices of acceptable quality it is important to recognize that this defect mechanism exists, and to take appropriate steps to detect unacceptable heating of the splice. We have developed a test technique for optical fiber splices that detects defective splices by measuring excessive optical absorption rather than optical scattering. Excessive optical absorption is detected by measuring heat generated at the fiber splice. The portion of the fiber that contains the pump pigtail splice is placed in a calorimeter. The pump laser is activated, and the thermal effects from optical absorption at the splice are allowed to reach equilibrium. The heat generated by this absorption is then measured. Readings above a threshold level indicate a defective splice. This technique can be used to evaluate the quality of any optical fiber splice but is especially adapted for measuring the pump pigtail splice of a dual clad cladding pump laser. This is due to the relatively high optical energy that is carried by the cladding. Defects that cause excessive optical absorption in a cladding layer are particularly harmful in this type of laser device.

The invention will be described in greater detail with the aid of the drawing.

DETAILED DESCRIPTION

Figure 1:
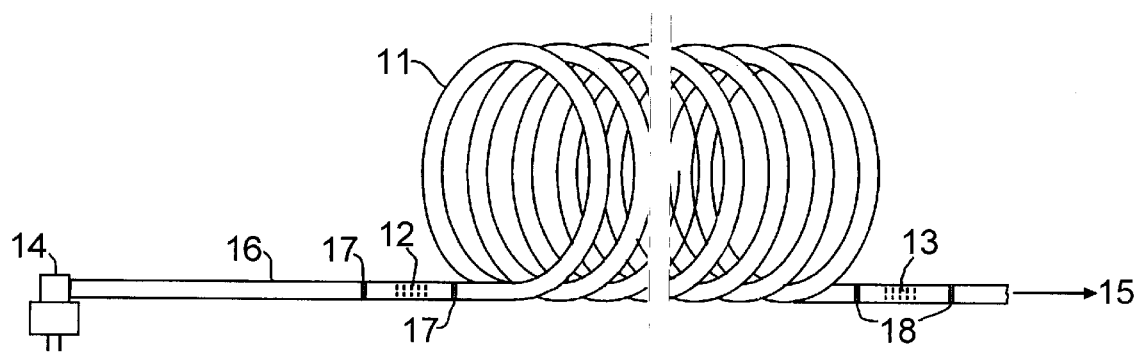
FIG. 1 is a schematic representation of a cladding pumped fiber laser device.

Referring to FIG. 1, a typical fiber laser structure is shown with optical fiber coil 11, with a portion of the coil cut away to depict substantial length. The length of the fiber in these structures is usually of the order of tens of meters, so the fiber in the figure represents many turns. The fiber can be supported on a mandrel or, because it is end-pumped (as shown), it can be strung out over its length or substantial portions of its length.

The laser cavity is formed by Bragg reflectors 12 and 13, shown here at the ends of the coiled fiber, These reflectors, or gratings, are typically produced by photoinducing refractive index changes in the core of the optical fiber. Preferably the core is appropriately sensitized with e.g. a hydrogen soak prior to writing the grating. The desired grating pattern is formed by using actinic radiation (typically an excimer laser—pumped frequency doubled dye laser operating near 240 nm) with a varying intensity or periodicity along the length of the fiber. This is conveniently done using a photomask, or by using a patterned light beam produced, e.g., by an interference pattern. The refractive index changes are produced typically by UV induced changes at defect sites of an absorbing ion such as germanium. The germanium doped fiber may be sensitized by hydrogen or deuterium treatments known in the art. Very large (>0.01) refractive index changes can be obtained in such a process. These techniques for forming optical gratings are well known in the art and are described in e.g. U.S. Pat. No. 4,725,110, issued Feb. 16, 1988 and U.S. Pat. No. 5,327,515, issued Jul. 5, 1994.

Referring again to FIG. 1, the fiber laser is end pumped by laser diode 14. The output of the fiber laser is indicated at 15. It will be evident to those skilled that the figures in this description are not drawn to scale, and the elements are schematically shown. The laser diode 14 is coupled to the active fiber portion via fiber pigtail 16. Grating 12 is spliced to the pigtail 16 and the active laser section 11 by splices 17, and grating 13 is spliced to the output end of the active laser section 11 by splices 18.

Figure 2:
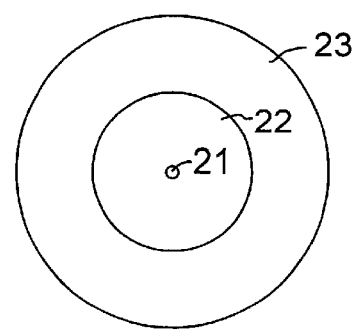
FIG. 2 is a section view of the optical fiber of the cladding pumped fiber laser device.

Referring to FIG. 2, a cross section of the fiber pigtail 16 is shown. This view is also representative of a cross section taken at any position along the active fiber laser. The fiber comprises core 21, first cladding 22, and second cladding 23.

The fiber is shown with a circular cross section but may be non-circular, i.e. slightly elliptical, to allow mode coupling. The core of the fiber 21 is germanium doped silica, with conventional additives to improve homogeneity. The first cladding layer 22 is typically a high silica material, preferably pure $SiO_2$ but at least 85% $SiO_2$. If desired the first cladding layer may include dopants, e.g. germanium, aluminum or phosphorus, to increase the refractive index of the cladding and reduce the Δ between the cladding and the core. In principle, this allows the core to be more heavily doped while still retaining the overall core/clad guiding characteristics desired. Another option is to reduce the Δ using the technique described in my copending patent application referenced above.

The second cladding 23 may be any suitable cladding material capable of confining the pump radiation in the first cladding layer, i.e. having a significant Δ with the first cladding layer. A significant A in this context is, e.g., >0.03. A preferred second cladding layer is one of many well known polymer coating materials, doped with fluorine to yield the requisite Δ. An advantage of this choice is that the second cladding layer also can also serve as the primary fiber coating. Examples of a suitable materials are UV-curable fluorinated acrylates.

The dimensions of the structure shown in FIG. 2 may vary substantially. The first cladding layer is typically in the range 50–400 $\mu$m, and preferably 100–300 $\mu$m. The second cladding layer thickness may range from 10 $\mu$m to several hundred $\mu$m. For light guiding purposes the layer can be relatively thin. If the second cladding layer also serves as the primary or the sole coating, a substantially greater thickness will generally be desired. The diameter of the core is typically of the order of 5–8 $\mu$m.

For ease and low loss in splicing the fiber laser section to the pump pigtail it is important that the core diameters closely match. The splice 17 may be a fusion splice or other conventional splice. Typically fiber sections are spliced together by removing the fiber coating from the ends to be spliced, and re-applying coating material to the splice region. In some cases the splice will have small defects, produced e.g. by foreign debris introduced during the coating removal and re-coating operation, or due to other factors such as non-precision alignment. These defects may act as light absorption centers and create excessive heating as outlined previously.

Figure 3:
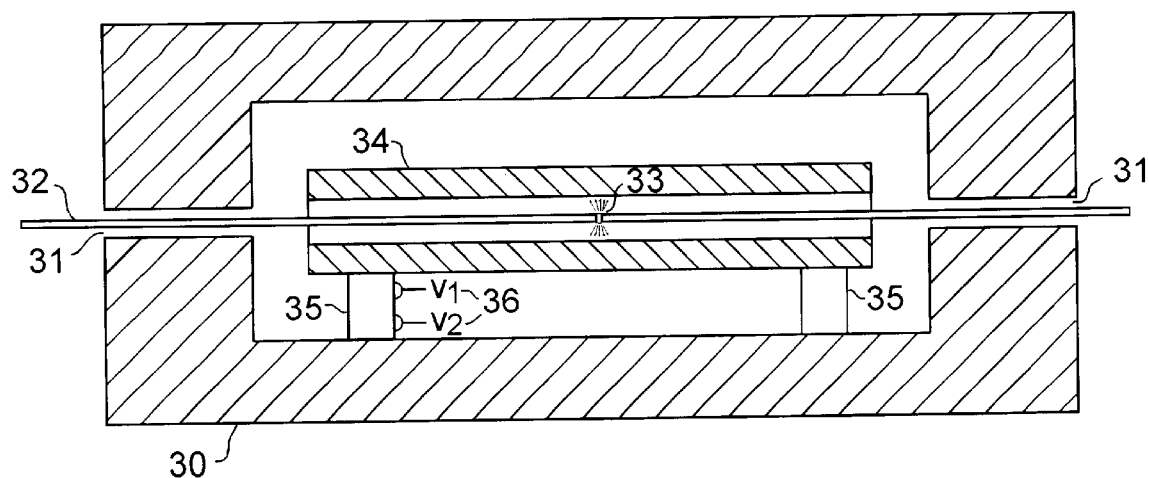
FIG. 3 is a schematic view of a test apparatus for the test technique of the invention.

To detect faulty splices according to the invention, the section of the fiber containing the splice is mounted in a calorimeter. A suitable calorimeter apparatus is shown in FIG. 3. Housing 30 is shown in section with openings 31 to accommodate the fiber section 32 to be tested. The splice being evaluated is shown at 33. The housing 30 may be of any suitable material, and preferably is constructed of a material with high heat conductivity, such as aluminum or copper, to provide effective heat sinking. It also preferably has a highly reflecting interior surface to reflect any stray radiation from the fiber splice onto the heat sensing element. This is especially useful if the heat sensor element is flat rather than cylindrical as shown in this embodiment. The heat sensor element 34 in FIG. 3 consists of a tubular length of heat absorbing and conducting material with low thermal inertia, such as copper foil. The inside surface of the heat sensor may be coated with a heat absorbing coating, e.g. black copper oxide. The heat sensor element 34 includes supporting legs 35, which for convenience may be extensions of the copper foil 34. Thermocouple heat monitors 36 are attached to the heat sensor element as shown. The thermocouples are arranged as a differential pair to detect heat flow along a portion of the sensor element.

To make the heat flow test measurement, light is introduced into fiber 32 by a pump laser in an arrangement like that shown in FIG. 1. The test may be performed on one or more fiber splices prior to final assembly, or may be made on splices of a finished and assembled laser device. In the cladding pumped device, a substantial portion of the laser radiation travels in the cladding and the coating so that unwanted absorption defects in these create the heat being measured. Scattered light from the splice that is incident on and absorbed by sensing element 34 may also contribute to the energy being measured but the objective of the technique described here is to measure the secondary emission that occurs as a result of light absorption, and is produced at long wavelengths, i.e. of the order of 10 $\mu$m.

The combination of low thermal inertia heat sensing element 34, and large heat sink 30, results in rapid equilibration of the heat flow from splice 33 along the heat sensing element. The difference in voltages $V_1$ and $V_2$ gives a rapid steady state measurement of the heat emanating from splice 33. The temperature difference may be converted to energy flow by calibrating the apparatus of FIG. 3 using a heating element with known power input in place of the optical fiber. The thermal resistance of the copper foil is calculated as the observed temperature difference divided by the electrical power. A threshold temperature difference indicated by $V_1$ and $V_2$ can be established empirically to signal a defective optical fiber splice. Splices that are found to produce excessive heat are easily repaired by cutting out the defective splice and re-splicing the fiber sections.

There is a trade-off between the time constant of the measurement and the sensitivity to heat flow. The time constant $\tau$ is determined by the product of the heat capacity C of the foil absorber and the thermal resistance R of the foil legs. Foil is preferably used as the heat sensor element to minimize the mass and therefore C. If the legs 35 are made wide, the time constant is shortened, thus minimizing $\tau$. However, high sensitivity to heat flow requires large R to maximize the temperature drop for a given heat flow. A compromise between sensitivity and time constant is reached with $\tau$ in the range 5–15 seconds, for which the sensitivity (1/R) is approximately 50 mW/°C. The minimum detectable energy flow is limited by the noise in the thermocouple reading with a comparable time constant and is typically 50 $\mu$W. This represents 0.02 $\mu$dB loss with 10 W of optical power in the fiber.

The differential thermocouple measurement gives a reliable indication of the heat generated at the optical fiber splice. With suitable calibration and empirical data, a single temperature measurement at any point in the heat transfer path may be used to indicate defective splices.

Figure 4:
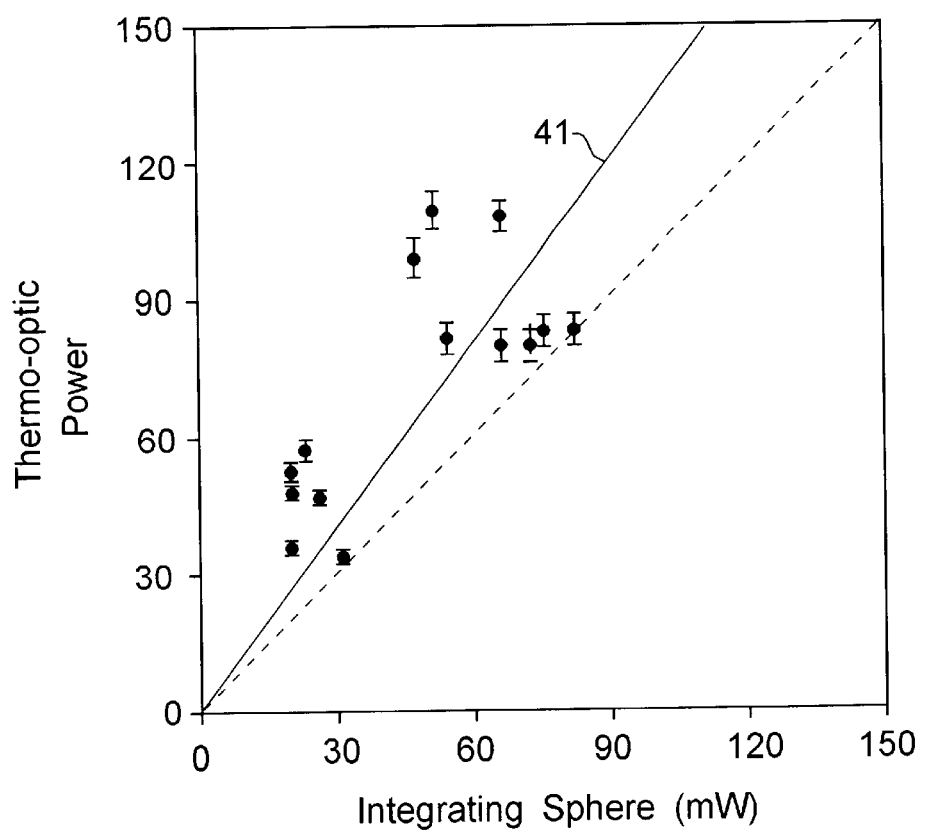
FIG. 4 is a plot of power ratios of optical vs. thermal power showing the advantage of thermal power measurements.

Measurements of optical fiber splices were made using the apparatus of FIG. 3 and are shown in the plot of FIG. 4. The dashed line is a reference line with a slope of one. The thermal power measurements are represented by line 41. These measurements consistently showed higher splice loss with thermo-optic power measurements than with integrating sphere (light only) measurements.

As indicated above the thermo-optic measurement of the invention may be made on one or more splices of a finished assembly or may be made at an intermediate stage of manufacture. For example, the gratings 12 and 13 in FIG. 1 may be produced, after the splices are successfully made and tested, by writing the gratings through the optical fiber coating.

The arrangement shown in FIG. 3 is given by way of example only of an apparatus that effectively measures heat generated at an optical fiber splice. The heat sensor 34 is but one suitable heat sensing element. A flat foil sensing element, with the optical fiber splice arranged near to or on the foil is an alternative arrangement. Others will occur to those skilled in the art.

Other heat measuring techniques may be used as well. A wide variety of calorimetric devices are known in the art. Any of these that have adequate sensitivity to detect power levels of the order of 1 mW may be used. The term calorimeter is used herein as defining any apparatus for measuring or detecting quantities or of absorbed or evolved heat.

It will be recognized that dual clad fiber for clad pumped lasers represents a special case in splice analysis and repair. Therefore, in the broad context the invention described above, effective power loss measurement of dual clad fiber may be in the form of light and/or heat. It should be understood that the term power loss measurement is inclusive in this regard.

The optical fiber splices described above are between two optical fiber sections. Splices between an optical fiber section and other optical elements such as lasers, modulators, optical integrated circuits, etc. may also be evaluated using the broader principles of the invention. The term optical element in this context includes devices like those just enumerated as well as optical fibers.

Since the measurement of the invention is a second order measurement, i.e. heat produced from absorbed light, there is a finite time required to generate the heat and for the heat transfer to the detector to reach equilibrium. It will be appreciated by those skilled in the art that an equivalent measurement cannot be made using a photodetector. A photodetector is an instantaneous measure of optical energy. The method of the invention requires bringing the calorimeter and the optical fiber splice to thermal equilibrium before the measurement is made, and typically involves an equilibrating period of more than one second, and usually more than five seconds.

The pump diode used in these demonstrations was a relatively broad band GaAlAs device. However, other semiconductor laser pump sources such as InGaAs or InGaAsP can be substituted. Semiconductor pump lasers are preferred but other pump sources, e.g. Nd-glass, Ti-sapphire, can be used.

The fiber laser structures described in this work are dual clad designs which facilitate end or cladding pumping. Single clad structures, which may also be side pumped, are also known in the art and could benefit from the teachings set forth above. The term cladding layer in the context of the invention means a layer that performs some light guiding function. In the dual clad structures described above the second cladding layer also functions as a protective layer, and in performing this function may be referred to as a fiber coating. However, dual cladding fiber laser structures of the kind described above may also have a coating in addition to the second cladding layer.

Various additional modifications of this invention will occur to those skilled in the art. All deviations from the specific teachings of this specification that basically rely on the principles and their equivalents through which the art has been advanced are properly considered within the scope of the invention as described and claimed.

I claim:

1. A method for evaluating an optical fiber splice between an optical fiber section and an optical element and wherein the optical fiber section has a core, a first cladding layer around the core, and a second cladding layer around the first cladding layer, and wherein the first cladding layer comprises a high silica glass, comprising the steps of introducing light radiation into the first cladding layer and measuring the power emanating from the optical fiber splice.

2. The method of claim 1 wherein the step of measuring the power emanating from the optical fiber splice includes measuring the thermal power.

3. A method for evaluating an optical fiber splice between two optical fiber sections comprising the steps of a. mounting the splice in a calorimeter, b. introducing laser radiation into one of the optical fiber sections, c. bringing the optical fiber splice and the calorimeter to thermal equilibrium, and d. measuring the thermal power emanating from the optical fiber splice.

4. The method of claim 3 wherein the optical fiber sections comprise dual clad optical fiber.

5. The method of claim 4 wherein the calorimeter comprises a metal foil heat sensing element and at least one thermocouple attached to the metal foil.

6. The method of claim 5 wherein the metal foil is a copper foil.

7. The method of claim 6 wherein the copper foil is coated with a heat absorbing layer.

\* \* \* \* \*